United States Patent [19]
Maley

[11] 3,974,269
[45] Aug. 10, 1976

[54] RADIOIMMUNE ASSAY METHOD FOR DETECTION OF GONORRHEA ANTIBODIES

[75] Inventor: Frank Maley, Delmar, N.Y.
[73] Assignee: Research Corporation, New York, N.Y.
[22] Filed: July 12, 1974
[21] Appl. No.: 487,971

[52] U.S. Cl. .............................. 424/1.5; 23/230 B; 195/103.5 R
[51] Int. Cl.² ...................... G21H 5/02; G01T 1/16; A61K 43/00
[58] Field of Search ................. 424/1, 12; 23/230 B; 195/103.5

[56] References Cited
OTHER PUBLICATIONS
Chemical Abstracts, vol. 77, 1972, p. 208, item No. 45159q.
Chemical Abstracts, vol. 79, 1973, p. 180, item No. 89163g.

*Primary Examiner*—Benjamin R. Padgett
*Assistant Examiner*—Christine M. Nucker
*Attorney, Agent, or Firm*—Cooper, Dunham, Clark, Griffin & Moran

[57] ABSTRACT

Gonorrhea antibodies in serum are detected by determination of radioactivity of conjugate formed between antibodies and antigens labelled with radioactive isotope.

11 Claims, 1 Drawing Figure

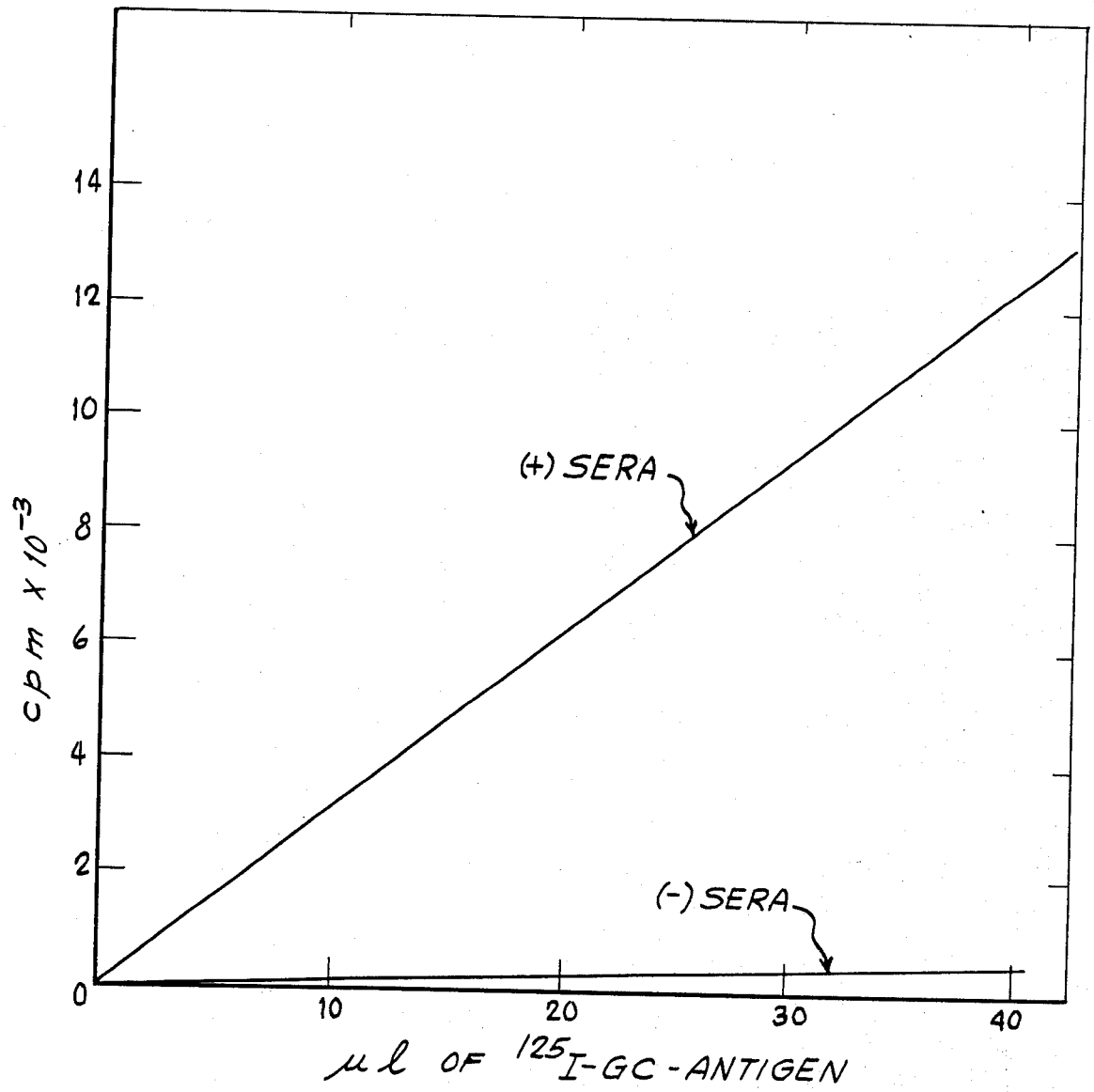

RADIOIMMUNE ASSAY METHOD FOR DETECTION OF GONORRHEA ANTIBODIES

RELATED APPLICATION

This application relates to improvements in the methods of detection disclosed in copending and commonly assigned patent application Ser. No. 385,863 filed on Aug. 6, 1973, the disclosure of which is hereby incorporated by reference.

FIELD OF INVENTION

This invention relates generally to methods for screening large number of persons for current or past gonorrhea infection.

Gonorrhea is one of the most commonly reported bacterial diseases in man and its persistence as a major health problem has intensified the search for new and better methods of detection.

The present mass screening method is a bacteriological method which requires two to seven days for completion. Moreover, it requires that a specimen of the gonorrhea caused discharge arrive at the testing laboratory with the fragile gonococcus organism still viable, a natural time limit of as little as two days.

In the above identified patent application, a novel serological method for detecting antibodies in sera is described. The method is generally based on the discovery and isolation of a heat labile antigen produced by Neisseria gonorrhoeae (N.g.) organisms. This antigen does not react with cross reacting antibodies which may also be present in the sera, with the result that the number of false positive reactions which have reduced the value of previously employed serological procedures is substantially reduced.

In accordance with the several detection methods described and claimed in the application, the antigens are caused to react with the antibody and the presence of the resulting complex is determined. In the principal methods described, the complex is caused to react with a labelled anti-human immunoglobulin G. The immunoglobulin is labelled with a fluorescent compound, a radioactive element, or an enzyme. The label is then detected by suitable procedures such as radioactive counting.

The optimum sources of the antigen are growth cultures of Neisseria gonorrhoeae ATCC 21823 (B-585), 21824 (B-370) and 21825 (B-1094), although a number of N.g. microorganisms will also serve as antigen sources.

Order: Eubacteriales
Family: Neissericeae
Genus: Neisseria
Species: Gonorrhoeae

Morphology: Gram negative spherical or bean shaped diplococci with adjacent sides flattened usually $0.6 \times 1.0 \mu$ and more uniform in size.

Biochemical and Cultural: Aerobic, optimal growth requires 4 – 10% $CO_2$ and incubation at 36°C.

The cultures grow slowly on chocolate agar producing small barely visible colonies after 24 hours (0.1 mm in diameter) with typical morphology seen on 48–72 hours cultures. The colonies are small 1.0 mm in diameter, gray white, transparent, smooth, with round entire edge, glistening surface and butyrous consistency. B-1094 produced slightly larger colonies and grows more rapidly.

Oxidase +, catalase +; ferments glucose but not maltose, lactose or sucrose.

Antigenicity: All three isolates share common antigens which is heat labile "L".

Virulence: All three strains were originally isolated from patients with symptomatic gonorrhea.

A novel radioimmunoassay technique has now been discovered which makes possible the detection of the antigen-antibody conjugate in a facile manner.

THE INVENTION

In accordance with the process of this invention, the presence of N.g. antibodies in serum is detected by a process which comprises the steps of:

A. Adding anti-human IgG to the serum to be tested in a buffered aqueous medium,
B. Thereafter adding a heat labile antigen which has been produced by a growth culture of N.g. and labeled with a radioactive element,
C. Incubating the resulting mixture at from about 4° to 45°C for from about 24 to 2 hours at a pH of from about 6.5 to 8.5 to form an antigen-antibody conjugate when said antibodies are present, and
D. Determining the level of radioactivity as a measure of the presence of the antigen-antibody conjugate.

The antigen which is used in this test is the heat labile antigen described in the above identified copending patent application. For the purpose of the test method which is described and claimed herein, the antigen is labelled with a radioactive element, the presence of which can be detected by ordinary means such as a counter.

The method of growth and isolation is as described below. The process is applicable to a number of N.g. organisms including those identified above by their ATCC numbers and to known organisms identified in our culture collection by the code designation B-273, B-125 and B-2169.

Cultures of N. gonorrhoeae B-370 are maintained in a lyophilized state or on semisolid medium and reconstituted as needed. Tissue culture bottles (29 oz.) containing 80 to 100 ml of a charcoal medium are inoculated with a sterile physiological saline suspension of cells, which had been grown for 18 hr. on rabbit chocolate agar slants at 35° in a 4 to 8% $CO_2$ atmosphere. After 18–24 hr., the cells are again suspended in saline and transferred to metal trays each containing about one liter of the charcoal medium. Following an overnight incubation, the cells are harvested by washing each tray with 150–200 ml of sterile physiological saline. The resulting suspension is filtered through sterile gauze and the filtrate centrifuged at 10,000 rpm in a Sorvall RC2-B centrifuge at 5° for 10 min.

The cell pellets are pooled, weighted and suspended in a solution of isotonic saline containing 0.3% sodium dodecyl sulfate (SDS), (4.0 ml/gm of cells wet wt.). This suspension is homogenized gently for 10 min. at room temperature, then centrifuged at 15,000 rpm for 10 min. The supernatant fraction is pooled and the cell pellets were reextracted with 0.1% SDS as before. The combined SDS supernatant fractions were centrifuged at 5,000 rpm to remove residual cells and were stored at 4° in 0.02% sodium azide. The antigenicity of these extracts, in addition to those purified by the following procedure, are monitored by a fluorescent inhibition assay described in the above identified copending application.

The combined SDS extracts concentrated at 4° to 15 mg/ml in an Amicon ultrafilter with a PM-10 membrane at 10 psi. Twenty ml of concentrate are applied to a 5.0 × 95-cm column of Bio-Gel A-5 m (100-200 mesh) which had been equilibrated previously in 0.05 M $NH_4HCO_3$ containing 0.01% sodium azide. Elution of the column is continued at 4° with this solution at a flow rate of 64 ml/hr. Fractions of 20 ml are collected and those containing the GC-antigen are combined (Fractions 35–45) and concentrated to 1 mg/ml of protein in an Amicon ultrafilter as described above.

The agarose column purified GC-antigen (6.6 mg of protein in 6.0 ml of 0.05 M $NH_4HCO_3$) is mixed with 0.5 mg of crystalline deoxyribonuclease and 0.25 mg crystalline ribonuclease and the resulting solution dialyzed for 24 hr. at 25° against two 2-liter changes of 0.05 M $NH_4HCO_3$, 0.01 M $MgCl_2$, and 0.01% sodium azide. Most of the protein is recovered as revealed by Lowry protein analysis but much of the nucleic acid is removed as indicated by a decrease in absorbance at 280 nm of 48% and of 67% at 260 nm. The nuclease-treated GC-antigen mixture is then chromatographed at 4° on a 2.0 × 42-cm column of Bio-Gel A-1.5 m (100–200 mesh) previously equilibrated with 0.05 M $NH_4HCO_3$. Fractions of 3.2 ml are collected at a flow rate of 9.6 ml/hr. The GC-antigen elutes as a single sharp peak at the void volume of the column (fractions 14–18) and is concentrated in an Amicon ultrafilter at 10 psi with a PM-10 membrane. The protein recovery is 60%.

The above partially purified GC-antigen is iodinated by a slight modification of the procedure of Syvanen et al. as described in *J. Biol. Chem.* 248, 3762 (1973) in which the following components are incubated at room temperature for 30 sec: 10 $\mu$l of 1 mM KI; 10 $\mu$l of $Na^{125}I$ (7.7 × 10 7 cpm); 10 $\mu$l of 1.5 mM chloramine T; and 2 $\mu$l of 1 N $H_2SO_4$. To this solution is added 25 $\mu$l of 0.5 N potassium phosphate, pH 7.1, and 0.1 ml of partially purified GC-antigen (44 $\mu$g of protein) containing 0.05% SDS. After an additional 2–4 min of incubation, 10 $\mu$l of 1 M2-mercaptoethanol is added and the resulting solution passed through a 0.9 × 26-cm column of Bio-Gel A 1.5 m (100–200 mesh). The column, equilibrated previously with 0.05 M potassium phosphate, pH 7.0, is developed with this buffer at a flow rate of 20 ml/hr. Fractions of 1.2 ml are collected. The iodinated GC-antigen elutes sharply between tubes 6–8 while $^{125}$ iodide ion elutes between tubes 13-18. To each 0.5 ml of the pooled GC-antigen was added 1.4 ml of 1% bovine serum albumin (BSA) containing 0.02 M EDTA and 0.1 ml of 1% sodium azide.

The antigen-antibody conjugate is formed by a reaction which takes place in an aqueous medium at a pH of from about 6.5 to 8.5 during a period of from about 24 to 2 hours at a temperature of from about 4°C to 45°C. Reaction is effected by mixing the serum under test with an aqueous buffer and adding anti-human IgG followed by the addition of the labelled antigen. The order of addition is most important and most unexpected. The normal procedure for the preparation of conjugates is to add the antigen to the serum and then to add the antihuman IgG. Unexpectedly, it has been discovered that with the heat labile antigen of this invention, the normal procedure is inapplicable, because the test is not sufficiently sensitive to distinguish between positive and negative sera with a useful degree of confidence. However, following the abnormal order of addition of this invention, the test is remarkably sensitive, reproducible and capable of detecting positive males and females at a percent of as high as 85% or higher.

The preferred buffer is phosphate buffered saline (PBS) because it is relatively inexpensive and reliable, although a number of other buffers may be employed. Typical of the well known buffers which may be employed in this invention are borate, glycine, pyrophosphate and imidazole buffers.

In a typical procedure for the detection of antibodies: 0.1 ml of phosphate buffered saline, pH 7.2; 5 $\mu$l of serum; 30 $\mu$l of sheep anti-human IgG (Meloy Labs., 6.4 mg antibody/ml); 10 to 20 $\mu$l of $^{125}$ I-labelled GC-antigen (3000–5000 cpm ) are mixed as described above. Even less than 5 $\mu$l of serum can be used, provided the amount of anti-human IgG added is adjusted to yield maximal precipitation of radioactivity. The antigenantibody reaction mixture is incubated at 45° for 2 hours and at the end of this period 0.50 ml of PBS was added. The PBS may be omitted, but is used to provide a larger volume of material to facilitate handling. The suspension is filtered through a 2.4-cm Whatman GF/C filter using a pyrex microanalysis filter apparatus.

The filter is prewashed to minimize nonspecific binding of antigen. The preferred prewash medium is bovine serum albumin although other reagents such as human serum immunoglobulin, ovalbumin and hemoglobin may also be employed. The preferred prewash is with 0.5 ml of a solution containing 2% by weight fraction V BSA together with a chelating agent such as 0.01 M ethylenediamine tetraacetic acid (EDTA).

After filtration, the precipitate is washed thoroughly with water. The radioactivity of the precipitate is then determined by any convenient method, for example a gamma spectrometer. Blank reactions, which contain all of the components of the reaction media except the serum, are also counted. These are subtracted from the results obtained with positive and negative sera. This procedure serves to reduce proportionately the low level of radioactivity fixed by the negative sera since the blank values often amount to half the count incorporated by the negative sera.

The filter procedure just described, while perfectly adequate for many purposes, is not preferred for large scale population screening. For this purpose, the centrifugation procedure is preferred. The incubation procedure employed is similar to the procedure utilized with the filter procedure except that the buffer contains a reagent to eliminate non-specific binding of the antigen. The reagent performs the same function in the incubation medium as it does in the filter procedure for washing the filter. The same reagents as mentioned above can be employed, and again BSA is preferred.

A typical incubation medium contains 0.2 ml of PBS containing 2% by weight BSA, 0.02 M EDTA or other chelating agent; 5 $\mu$l of serum; 30 $\mu$l of sheep anti-human IgG and 10 to 20 $\mu$l of $^{125}$I labelled antigen.

Following incubation of the typical incubation medium, 3 ml of PBS are added to the reaction mixture which is then centrifuged at from about 2000 to 3000xg. The supernatant fractions are discarded and the centrifugation tube again washed with 3 ml of PBS and recentrifuged. The supernatant is discarded and the precipitate counted, for example with a gamma counter.

Of course, as in the filter procedure, other buffers can be employed in the centrifugation process. In both procedures the chelating agent can be omitted.

While the procedure has been described with $^{125}$I as the detectable element, others may also be utilized, for example $^{14}$C-acetic anhydride, maleic anhydride, fluorodinitro benzene, fluorescein, and isothiocyanate; $^{32}$P-diisopropylfluorophosphate; and $^{35}$S phenylisothiocyanate. The preferred detectable element is $^{125}$I because a scintillation solution is not required if it is used in a gamma ray spectrometer, and it is a weak enough gamma emitter with a sufficiently short half life to obviate much of the hazzard of working with it.

A comparison of the reactivity of known positive and negative sera using the filter assay procedure is presented in FIG. 1 and as indicated, the reaction is directly proportional to the quantity of antigen added. Depending on the antigen preparation and the quantity of gonococcal antibodies in the sera used, the ratio of labeled antigen fixed by positive sera to that of negative sera may vary from 10/1 to 30/1.

It is important, although not essential, to add the GC-antigen to each sample at about the same time, that is within about 2 minutes following the sheep anti-human IgG because the extent of antigen precipitation is related to its time of addition. Thus, is added 60 min after the sheep anti-human IgG, antigen fixation is reduced by almost half. In contrast, if the antigen is added to negative sera just prior to the anti-human IgG, excessively high values are obtained which in effect reduces the positive to negative ratio to about 3 to 1. However, these factors can be compensated for if for some reason it is desirable or necessary to withhold prompt addition of the GC-antigen.

Normally duplicate reactions containing no more than 3000 to 6500 cpm of labelled GC-antigen are adequate to distinguish between positive and negative sera. Comparisons are made with blanks or with negative pools or sera. The optimum procedure is to prepare a titration curve similar to FIG. 1. Usually a serum may be considered positive if it fixes three times the level of antigen fixed by a negative pool.

To establish the sensitivity and specificity of this method, 152 sera (57 men and 95 women) were examined in a double-blind study. Only sera from patients with a bacteriologically confirmed diagnosis of gonorrhea were considered positive, while the negative controls were obtained from individuals with negative-bacteriological and clinical findings.

As indicated in Table 1, the process of this invention provides a high degree of reliability in detecting gonorrhea in males and females, Thus, it was possible to correctly identify 87% of the infected men and 88% of the infected women. False positives were encountered in only three cases. Included in the test were 20 duplicates and 2 triplicates, and in no instance was there a discrepancy among these results. The inability to detect positive cases in some instances is not surprising, since antibody titers may not have reached detectable levels at the time the serum samples were taken.

TABLE 1

COMPARISON OF CULTURE AND CASE HISTORY DIAGNOSES FOR GONORRHEA WITH THE RADIOIMMUNE ASSAY

| Sex | Determined Positive | | | Determined Negative History and | | |
|---|---|---|---|---|---|---|
| | Culture | RIA | Percent | Culture | RIA | Percent |
| Male | 38 | 33 | 87 | 19 | 17 | 90 |
| Female | 60 | 53 | 88 | 35 | 34 | 97 |

What is claimed is:

1. A radioimmunoassay method for determining the presence of *Neisserria gonorrhoeae* antibodies in human serum which comprises the steps of:
   A. adding anti-human IgG to the serum to be tested in a buffered aqueous medium,
   B. thereafter adding a heat labile antigen which has been produced by a growth culture of *Neisseria gonorrhoeae*, isolated therefrom, and labelled with a detectable radioactive element,
   C. incubating resulting mixture at from about 4°C to 45°C for from about 24 to 2 hours at a pH of from about 6.5 to 8.5 to form an antigen-antibody conjugate when said antibodies are present, and
   D. determining the level of radioactivity as a measure of the presence of said antigen-antibody conjugate.

2. A method as in claim 1 wherein the radioactive element is $^{125}$I.

3. A radioimmunoassay method for determining the presence of *Niesseria gonorrhoeae* antibodies in human serum which comprises the steps of:
   A. adding anti-human IgG to the serum to be tested in a buffered aqueous medium,
   B. thereafter adding a heat labile antigen which has been produced by a growth culture of *Neisseria gonorrhoeae*, isolated therefrom, and labelled with a detectable radioactive element,
   C. incubating resulting mixture at from about 4°C to 45°C for from about 24 to 2 hours at a pH of from about 6.5 to 8.5 to form an antigen-antibody conjugate when said antibodies are present,
   D. filter resulting mixture through a filter which has been previously washed with a reagent selected from the group consisting of bovine serum albumin, human serum immunoglobulin, ovalbumin, and hemoglobin to separate said antigen-antibody conjugate, and
   E. determining the level of radioactivity in resulting precipitate as a measure of the presence of said antigen-antibody conjugate.

4. A method as in claim 3 wherein the radioactive element is $^{125}$I.

5. A method as in claim 3 wherein the reagent utilized in Step D is bovine serum albumin.

6. A method as in claim 3 wherein the radioactive element is $^{125}$I and the reagent utilized in Step D is bovine serum albumin.

7. A radioimmunoassay method for determining the presence of *Neisseria gonorrhoeae* antibodies in human serum which comprises the steps of:
   A. adding anti-human IgG to the serum to be tested in a buffered aqueous medium containing a reagent selected from the group consisting of bovine serum albumin, human serum immunoglobulin, ovalbumin, and hemoglobin,
   B. thereafter adding a heat labile antigen which has been produced by a growth culture of *Neisseria gonorrhoeae*, isolated therefrom, and labelled with a detectable radioactive element together with bovine serum albumin, C. incubating resulting mixture at from about 4°C to 45°C for from about 24 to 2 hours at a pH of from about 6.5 to 8.5 to form an antigen-antibody conjugate when said antibodies are present, D. diluting resulting mixture with an aqueous buffer and centrifuging, and E. determining the level of radioactivity in resulting precipitate as a measure of the presence of said antigen-antibody conjugate.

8. A method as in claim 7 wherein the reagent is bovine serum albumin.

9. A method as in claim 7 wherein the radioactive element is $^{125}I$.

10. A method as in claim 7 wherein the buffer is phosphate buffered saline.

11. A method as in claim 7 wherein the reagent is bovine serum albumin, the radioactive element is $^{125}I$ and the buffer is phosphate buffered saline.

* * * * *